(12) United States Patent
Dragon

(10) Patent No.: US 10,740,905 B2
(45) Date of Patent: Aug. 11, 2020

(54) SYSTEM FOR DYNAMICALLY MAXIMIZING THE CONTRAST BETWEEN THE FOREGROUND AND BACKGROUND IN IMAGES AND/OR IMAGE SEQUENCES

(71) Applicant: uniqFEED AG, Zürich (CH)

(72) Inventor: Ralf Dragon, Hannover (DE)

(73) Assignee: uniqFEED AG, Zürich (CH)

( * ) Notice: Subject to any disclaimer, the term of this patent is extended or adjusted under 35 U.S.C. 154(b) by 0 days.

(21) Appl. No.: 16/341,824

(22) PCT Filed: Oct. 9, 2017

(86) PCT No.: PCT/EP2017/075624
§ 371 (c)(1),
(2) Date: Apr. 12, 2019

(87) PCT Pub. No.: WO2018/069219
PCT Pub. Date: Apr. 19, 2018

(65) Prior Publication Data
US 2020/0090341 A1    Mar. 19, 2020

(30) Foreign Application Priority Data
Oct. 14, 2016   (DE) .......................... 10 2016 119 639

(51) Int. Cl.
*G06T 7/194* (2017.01)
*H04N 5/765* (2006.01)
(Continued)

(52) U.S. Cl.
CPC ............ *G06T 7/194* (2017.01); *G06T 7/0002* (2013.01); *G06T 7/11* (2017.01); *G06T 7/143* (2017.01);
(Continued)

(58) Field of Classification Search
USPC .................................. 386/223–224, 278–290
See application file for complete search history.

(56) References Cited

U.S. PATENT DOCUMENTS 5,731,846 A    3/1998  Kreitman et al.
6,292,227 B1   9/2001  Wilf et al.
(Continued)

FOREIGN PATENT DOCUMENTS

DE    102004011629 A1    10/2004
EP       0683961 A1       11/1995
(Continued)

OTHER PUBLICATIONS

"Location Android Developer", https://web.archive.org/web/20140701065849/http://developer.android.com/reference/android/location/Location.html, Aug. 5, 2015, pp. 1-8.
(Continued)

*Primary Examiner* — Hung Q Dang
(74) *Attorney, Agent, or Firm* — Murphy, Bilak & Homiller, PLLC

(57) ABSTRACT

The invention relates to a system for dynamically maximizing the contrast between the foreground and background in images and/or image sequences, comprising at least one image capturing device (C1, C2), at least one analysis module (A1, A2) which is connected to the image capturing device (C1, C2) and which is designed to determine a transformation between a two-dimensional coordinate system of the image capturing device (C1, C2) and a two-dimensional coordinate system of a display device (L) and carry out a segmentation in order to determine at least the occlusion of background objects by means of foreground objects in an image; at least one control module (K) which is connected to the analysis module (A1, A2); and at least one display device (L) which is designed to display display information, in particular video clips, wherein the image
(Continued)

Figure 1:
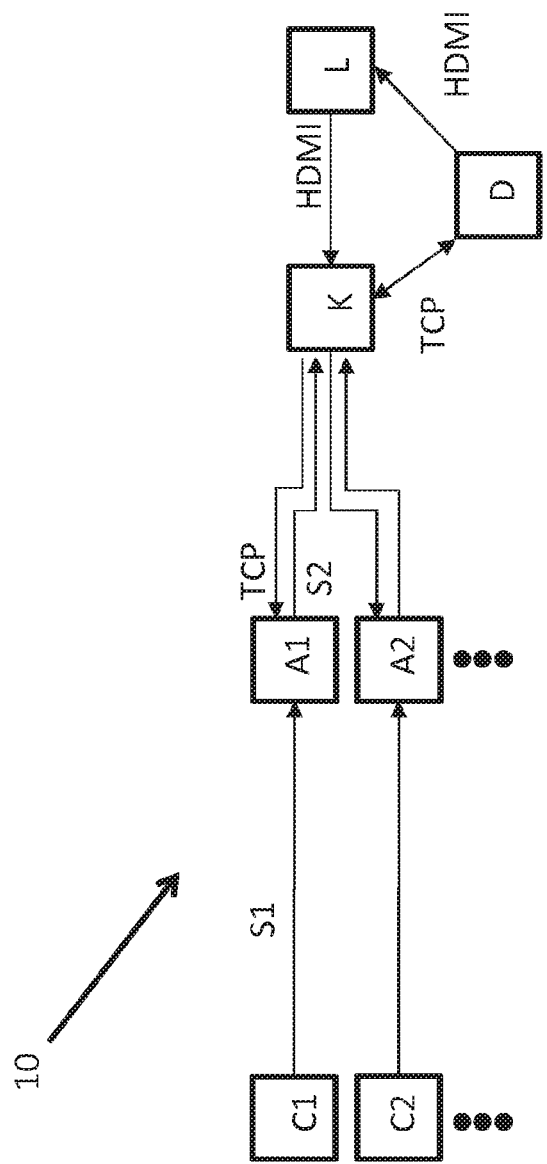

capturing device (C1, C2) is designed to capture the display information displayed on the display device (L), the analysis module (A1, A2) is additionally designed to ascertain quality data relating to the segmentation and transmit same to the control module (K), and the control module (K) is designed to adapt the display information displayed on the display device (L) on the basis of the quality data.

17 Claims, 1 Drawing Sheet

(51) Int. Cl.
| | |
|---|---|
| *G06T 7/00* | (2017.01) |
| *G06T 7/143* | (2017.01) |
| *G06T 7/11* | (2017.01) |
| *H04N 5/222* | (2006.01) |
| *H04N 21/81* | (2011.01) |
| *G16B 20/00* | (2019.01) |
| *G11B 27/031* | (2006.01) |

(52) U.S. Cl.
CPC ... *H04N 5/765* (2013.01); *G06T 2207/10016* (2013.01); *G06T 2207/10024* (2013.01); *G06T 2207/30168* (2013.01)

(56) References Cited

U.S. PATENT DOCUMENTS

| | | | |
|---|---|---|---|
| 6,384,871 | B1 | 5/2002 | Wilf et al. |
| 7,158,666 | B2 | 1/2007 | Deshpande et al. |
| 9,892,538 | B1* | 2/2018 | Balasubramanian ... G06T 11/60 |
| 2003/0001954 | A1 | 1/2003 | Rantalainen et al. |
| 2004/0085342 | A1 | 5/2004 | Williams et al. |
| 2006/0026628 | A1 | 2/2006 | Wan et al. |
| 2010/0277468 | A1 | 11/2010 | Lefevre et al. |
| 2012/0033032 | A1 | 2/2012 | Kankainen |
| 2013/0050294 | A1 | 2/2013 | Hubo |
| 2013/0249900 | A1 | 9/2013 | Lee et al. |
| 2015/0007218 | A1 | 1/2015 | Neumann et al. |
| 2015/0163416 | A1 | 6/2015 | Nevatie |
| 2015/0206349 | A1 | 7/2015 | Rosenthal et al. |
| 2016/0028968 | A1 | 1/2016 | Affaticati |
| 2016/0217604 | A1 | 7/2016 | De Roos et al. |
| 2016/0226253 | A1 | 8/2016 | Abido et al. |
| 2016/0227275 | A1* | 8/2016 | Vuori ............... G06K 9/00744 |
| 2016/0373814 | A1 | 12/2016 | Kellner |
| 2017/0237910 | A1* | 8/2017 | Salin ............... H04N 5/272 |
| | | | 345/634 |

FOREIGN PATENT DOCUMENTS

| | | |
|---|---|---|
| EP | 1071278 A2 | 1/2001 |
| EP | 2463821 A1 | 6/2012 |
| EP | 2498489 A1 | 9/2012 |
| EP | 2822288 A1 | 1/2015 |
| FR | 2959339 A1 | 10/2011 |
| GB | 2408164 A | 5/2005 |
| KR | 20130022491 A | 3/2013 |
| KR | 20130115332 A | 10/2013 |
| WO | 9631047 A2 | 10/1996 |
| WO | 9712480 A2 | 4/1997 |
| WO | 2014031899 A1 | 2/2014 |

OTHER PUBLICATIONS

Abawi, Daniel F, et al., "Accuracy in Optical Tracking with Fiducial Markers: An Accuracy Function for ARToolKit", Proceedings of the Third IEEE and ACM International Symposium on Mixed and Augmented Reality (ISMAR 2004), 2004, pp. 1-2.

Hallaway, Drexel, et al., "Bridging the Gaps: Hybrid Tracking for Adaptive Mobile Augmented Reality", Applied Artificial Intelligence; vol. 18, No. 6, Jul. 1, 2004, pp. 477-500.

Jain, Ramesh, et al., "Metadata in Video Databases", ACM SIGMOD Record., vol. 23, No. 4, Dec. 1994, pp. 27-33.

Lindner, Manfred, "Content Management—technische Aufbereitung, Transport und Präsentation von Daten", Elektrotechnik und Informationstechnik. Heft 7/8, Jul./Aug. 2003, pp. 245-250.

Lu, Boun Vinh, et al., "Foreground and Shadow Occlusion Handling for Outdoor Augmented Reality", 9th IEEE International Symposium, 2010, pp. 109-118.

Paulevé, Loic, et al., "Locality sensitive hashing: A comparison of hash function types and querying mechanisms", Pattern Recognition Letters, Bd. 31, H. 11, 2010, pp. 1348-1358.

Segal, Mark, et al., "The OpenGL Graphics System: A Specification (Version 1.2.1)", Silicon Graphics, Inc., Oct. 14, 1998, pp. 1-278.

Shepard, Daniel P., et al., "Precise Augmented Reality Enabled by Carrier-Phase Differentiated GPS", 25th International Technical Meeting of the Satellite Division of the Institute of Navigation, Nashville, TN, Sep. 17-12, 2012, pp. 3169-3184.

Sun, Jiande, et al., "Unequally Weighted Video Hashing for Copy Detection", Advances in Multimedia Modeling; 19th International Conference, MMM; Huangshan, China, Jan. 7-9, 2013, pp. 546-557.

Weng, Li, et al., "From Image Hashing to Video Hashing", Advances in Multimedia Modeling; 16th International Conference, MMM, Chongqing, China, 2010, pp. 662-668.

Xu, Changsheng, et al., "Implanting Virtual Advertisement into Broadcast Soccer Video", Pacific-Rim Conference on Multimedia, 2004, LNCS 3332; Springer-Verlag Berlin Heidelberg, 2004, pp. 264-271.

* cited by examiner

SYSTEM FOR DYNAMICALLY MAXIMIZING THE CONTRAST BETWEEN THE FOREGROUND AND BACKGROUND IN IMAGES AND/OR IMAGE SEQUENCES

The invention relates to a system for dynamically maximizing the contrast between foreground and background in images and/or image sequences.

For the smooth integration of virtual objects into real scenes (also called augmented reality), it is known that there are two problems to solve. On one hand, the transformation between camera coordinate system and scene coordinate system must be determined and, on the other hand, occlusions of virtual objects, which are usually displayed in the background, must be determined by real objects, which usually are in the foreground.

In the application area "television transmission" or "broadcasting", one is interested in solving the two aforementioned problems preferably non-mechanically, i.e. without the additional use of markers or sensors. This allows for a shorter assembly time and reduces the complexity of a broadcast system on site to be assembled as a whole. Especially with live broadcasts, the majority of the equipment must be transported to the usage site and subsequently assembled and disassembled.

To solve the transformation problem, there are, on one hand, hardware-based solutions such as "encoded heads" (e.g. from vinten.com), and, on the other hand, software-based, visually working solutions. Both solutions provide a mapping x=M(X) which allows to map a 3D coordinate X of a virtual object in the 3D space in a camera coordinate x in the current camera image.

Previously known segmentation methods require so-called keying instructions, such as a specific background color (e.g., in the case of chroma keying or infrared keying). However, these mechanical solutions have the above-mentioned disadvantages, since the keying instructions must be installed at the transmission site.

Object of the invention is to avoid the above disadvantages.

To solve this object, a system for dynamically maximizing the contrast between foreground and background in images and/or image sequences is suggested, comprising
at least one image-recording device,
at least one analysis module connected to the image-recording device, which is configured to determine a transformation between a two-dimensional coordinate system of the image-recording device and a two-dimensional coordinate system of a display device, and carry out a segmentation in order to determine at least occlusions of background objects through foreground objects in an image,
at least one control module connected to the analysis module,
at least one display device, which is configured to display display information, in particular, video clips, wherein the image-recording device is configured to record the display information displayed on the display device,
wherein the analysis module is further configured to identify quality data on the segmentation and transmit same to the control module, and
wherein the control module is configured to adjust the display information displayed on the display device based on the quality data.

By taking into account quality data on the segmentation, it is possible to obtain information about whether foreground and background are in sufficient contrast to each other. In case of a non-sufficient contrast, the display information can be adjusted, so that in the case of an unchanged foreground, a high-contrast background can be generated.

The system can further include a database, which is connected to the control module and to the display device, wherein the database is configured to store a sequence of display information to be displayed on the display device one after the other. The database can, for example, be part of a media server. The media server transmits display information to be played, for example, video clips, to the display device.

In this connection, it is preferred that the control module is configured to change the stored sequence of the display information. In other words, the control module can instruct the media server to output or display a particular piece of display information on the display device. To achieve optimum control by means of the control module, the display information output from the media server on the display device (video clip) can also be transmitted to the control module.

The analysis module can be configured to apply and minimize an energy function during the segmentation, wherein the energy function is based on probability distributions of foreground objects and background objects and/or on pixel-wise probability distributions. The segmentation into foreground and background (with intermediate values such as semi-occlusions or blurring being possible) is designated with Y.

Here segmentation methods are used that do not require keying instructions, but can separate arbitrary background and foreground objects. In this process, an energy function E(Y) is defined, which is to be minimized. E(Y) can correspond to the negative logarithm of the probability that an occlusion has been determined correctly. Methods of convex optimization permit to minimize the energy efficiently and optimally, taking into account each individual image point, i.e. to maximize the corresponding probability. However, for minimizing the energy function E(Y), a priori knowledge of the appearance of the background and of the foreground is required, in particular, in the form of probability distributions F (foreground) and B (background) or pixel-wise distributions $f\_i$ and $b\_i$, wherein i designates a specific image point/pixel.

This a priori knowledge needs to be updated due to possible changes in brightness or changes of the appearance, which causes drifting (the progressive deviation of a model from reality). Due to the above-described feedback mechanism, in which quality data on the segmentation are transmitted to the control module, and the control module adjusts the display information based on the quality data, the drift problem can be counteracted. This allows therefore the use of current segmentation methods with enhanced performance. The feedback takes, in particular, place via the display device, preferably an LED system as it, for example, exists for banner advertising in many sporting events.

The control module can be further configured to determine for remaining display information of the sequence, in which display information an expected probability distribution of the foreground and an expected probability distribution of the background of the image-recording device differ the most.

The control module can also be configured to calculate a probability mapping for a respective image-recording device, wherein the probability mapping describes which probability distribution exists in an image of the respective image-recording device if the display device displays any one of the remaining pieces of display information.

The control module can be further configured to determine the probability mapping based on the time-varying 2D-2D mapping x=F(d) between d in the coordinate system of the display device and x in the coordinate system of the image-recording device. This 2D-2D mapping F can, for example, be determined by applying x=M(X), wherein X is the physical position X of the display point d.

The control module can be configured to determine the probability mapping based on a radiometric calibration between the display device and the respective image-recording device.

On the display device a plurality of arbitrarily designed calibration marks can be arranged, which are detectable by the image-recording device, in order to facilitate the 2D-2D transformation F between the coordinate system of the display device and the coordinate system of the image-recording device. In order that such calibration marks need not be regularly assembled and disassembled, the display devices can have such calibration marks permanently. The calibration marks can also be designed in such a manner that a radiometric calibration between recording device and display is possible.

The control module can be further configured to insert calibration information into the sequence of display information, wherein the display device is configured to display the calibration information. In this process, the calibration information can comprise at least a single monochrome image, wherein the image has a display duration of at least one or precisely one frame, and wherein the image preferably has a color, which has a high contrast to a foreground object. If a piece of calibration information is displayed as a monochrome image for the duration of a frame on the display device only, the calibration information is not visible to a viewer of the display device with the naked eye. However, the calibration information displayed on the display device is recorded by the image-recording device, so that the respective frame can be used to update knowledge of foreground objects and background objects, as it is known for this frame, which color the background has.

The aforementioned problem is also solved by a method for dynamically maximizing the contrast between foreground and background in images and/or image sequences, comprising the steps of:

detecting at least one image by means of at least one image-recording device, calculating a transformation between a two-dimensional coordinate system of the image-recording device and a two-dimensional coordinate system of the display device, carrying out a segmentation in order to determine at least occlusions of background objects through foreground objects in an image, displaying display information, in particular, video clips, on a display device, wherein the display information displayed on the display device is recorded by the image-recording device, wherein, during segmentation, quality data on the segmentation are identified, and the display information displayed on the display device are adjusted based on the quality data.

This method can comprise further optional steps corresponding to the features described above for the system. Accordingly, further optional aspects of the method can be directly derived from these features.

In the following text, the invention is exemplarily and non-restrictingly described with reference to the accompanying FIGURES.

FIG. 1 shows a schematic diagram of the system presented herein.

A system 10 for dynamically maximizing the contrast comprises a plurality of image-recording devices C1, C2, Ck (indicated by three black dots below C2) and a plurality of analysis modules A1, A2 to Ak (indicated by three black dots below A2). An analysis module A1, A2 is assigned to each camera C1, C2.

The cameras C1, C2, Ck pass on appropriate data $S1k$ to the respective analysis module A1, A2, Ak. The analysis modules A1, A2, Ak determine (1) the current 2D-2D mapping F1, F2, Fk between a 2D coordinate in the display coordinate system of L in the image coordinate system of the respective camera C1, C2, Ck and (2) image point-wise occlusion. The data $S1k$ are, depending on the analysis module, purely optical, but can also include sensor data from step sensors, acceleration sensors, etc. The mapping Fk may have been calibrated manually or with an automatic calibration procedure.

The output data $S2k$ of the analysis modules A1, A2, Ak describe the specific mappings Fk as well as meta data on the occlusion. These output data are transmitted to a control module K.

Meta information to enhance the segmentation flows in the other direction (indicated by the arrows TCP) from the control module K to the analysis modules Ak.

Furthermore, the control module K is connected, via a network, to a database, D, in which display information (video clip) is stored, which can be displayed on the LED system L. The control module has, in particular, control access over the network on a media server with a video clip database D. The media server sends video clips to be played or display information Z to the LED system L.

The control module K is configured to instruct the media server to output certain display information or video clips Z, via an image transport protocol BP, e.g. via HDMI, SDI, DisplayPort or SDI over TCP, to the display device L. For control, the currently output video image is returned again to K via BP.

In particular, the setup should be noted with which the control module K selects the video material (display information) that is to be displayed on the display device L, as well as the control loop with feedback to the camera C1, C2. Usually, the video material (video clips) is organized a priori in a playlist, which is played during a broadcast of an event, such as a match in a specific sport, without the possibility of adaptation.

In the present case, the control module K is configured to dynamically adjust a sequence R of remaining display information or video clips Z, in order to obtain preferably good segmentation results.

For this purpose, a metric on the quality (quality data) of the segmentation is transmitted in the metadata $S2k$, for example, the segmentation energy $Ek(L)$ resulting after minimization. If this energy exceeds an acceptable level in one or more cameras C1, C2, Ck, the video clip order of the remaining sequence of video clips is dynamically adjusted. As already mentioned in the introduction, segmentation methods are used that do not require keying instructions, but can separate arbitrary background and foreground objects. In this process, an energy function $E(Y)$ is defined, which is to be minimized. $E(Y)$ can correspond to the negative logarithm of the probability that an occlusion has been determined correctly. Methods of convex optimization permit to minimize the energy efficiently and optimally, taking into account each individual image point, i.e. to maximize the corresponding probability. However, for minimizing the energy function $E(Y)$ a priori knowledge of the appearance of the background and of the foreground is required, in particular, in the form of probability distributions F (foreground) and B (background) or pixel-wise distributions f_i and b_i.

In the following equation, 1 designates the analysis module, where the remaining energy Ek(Yk) is the greatest, i.e. the segmentation is most likely not correct or most uncertain. This is an indication of a poor contrast between foreground and background.

$$1 = \arg\_k \max Ek(Yk)$$

Accordingly, the image G1(Z) is, for example, determined for the selected camera C1, which describes which probability distribution (at which pixel) is present in the camera image of C1, when the LED system L plays the display information or the video clip Z. G1 considers the 2D-2D mapping F1 from the LED system L to the camera C1 and background information of a radiometric calibration from the LED system L to the camera C1.

For every potential video clip Zm (display information) remaining in the sequence, the mapping G1(Zm) is determined. That clip Zn is played next where the probability distribution F1 of the foreground of camera C1 and the expected probability distribution G1 of the background of camera C1 differ the most:

$$n = \arg\_m \max d(F1, G1(Zm))$$

A metric d for the comparison of foreground and background distribution is, for example, the Kullback-Leibler divergence.

The system 10 described herein and associated method steps allow to periodically, i.e. when the remaining energy Ek increases due to inaccurate knowledge, update knowledge of foreground and background appearance in each camera image and thus actively prevent drifting (the progressive deviation of a model from reality).

The display device L described herein can be an LED system, for example, in the form of advertising banners. LED systems L internally have a control box, which receives appropriate prepared video signals via an image transport protocol, e.g. HDMI or the like. Furthermore, LED systems have a plurality of so-called cabinets, which can each constitute a small part of the entire image and are connected to the control box. In this process, the control box passes on an image section of the original video to each cabinet. For simplicity, it can be assumed that an LED system corresponds to a regular screen, except that the structure of an LED system can be significantly more flexibly designed, e.g., that no rectangular layout must be selected.

It should be noted that the system 10 described herein can also be part of a superordinate television broadcast system, as described in the application entitled "Television broadcast system for generating augmented images" filed by the same applicant on the same day. The control module described herein can be contained in the system described therein in the control module 18. The display device described herein can be contained in the LED system 20 described therein.

The invention claimed is:

1. A system for dynamically maximizing the contrast between foreground and background in images and/or image sequences, comprising
at least one image-recording device;
at least one analysis module connected to the at least one image-recording device and configured to determine a transformation between a two-dimensional coordinate system of the at least one image-recording device and a two-dimensional coordinate system of at least one display device, and carry out a segmentation to determine at least occlusions of background objects through foreground objects in an image;
at least one control module connected to the at least one analysis module; and
a database connected to the at least one control module and to the at least one display device,
wherein the database is configured to store a sequence of display information to be displayed on the at least one display device one after the other,
wherein the at least one display device is configured to display information, including video clips,
wherein the at least one image-recording device is configured to record the display information displayed on the at least one display device,
wherein the at least one analysis module is further configured to identify quality data on the segmentation and transmit the quality data to the at least one control module,
wherein the at least one control module is configured to adjust the display information displayed on the at least one display device based on the quality data,
wherein the at least one control module is configured to determine for remaining display information of the sequence, in which display information an expected probability distribution of the foreground and an expected probability distribution of the background of the image-recording device differ the most.

2. The system of claim 1, wherein the at least one control module is configured to change the stored sequence of the display information.

3. The system of claim 1, wherein the at least one control module is configured to calculate a probability mapping for a respective image-recording device, and wherein the probability mapping describes which probability distribution exists in an image of the respective image-recording device if the at least one display device displays any one of the remaining pieces of display information.

4. The system of claim 3, wherein the at least one control module is configured to determine the probability mapping based on a transformation between the coordinate system of the at least one display device and the coordinate system of the at least one image-recording device.

5. The system of claim 4, wherein the at least one control module is configured to determine the probability mapping based on a radiometric calibration between the at least one display device and the respective image-recording device.

6. The system of claim 4, wherein a plurality of calibration marks are arranged on the at least one display device, which are detectable by the at least one image-recording device to facilitate the transformation between the coordinate system of the at least one display device and the coordinate system of the at least one image-recording device.

7. The system of claim 1, wherein the at least one control module is configured to insert calibration information into the sequence of display information, and wherein the at least one display device is configured to display the calibration information.

8. The system of claim 7, wherein the calibration information comprises at least a single monochrome image, wherein the image has a display duration of at least one or precisely one frame, and wherein the image has a color having a high contrast to a foreground object.

9. The system of claim 1, wherein the at least one analysis module is configured to apply and minimize an energy function during segmentation, and wherein the energy function is based on probability distributions of foreground objects and background objects and/or on pixel-wise probability distributions.

10. The system of claim 9, wherein the at least one control module is configured to determine for remaining display information of the sequence, which display information an expected probability distribution of the foreground and an expected probability, distribution of the background of the image-recording device differ the most.

11. The system of claim 10, wherein the at least one control module is configured to calculate a probability mapping for a respective image-recording device, and wherein the probability mapping describes which probability distribution exists in an image of the respective image-recording device if the at least one display device displays any one of the remaining pieces of display information.

12. The system of claim 11, wherein the at leak one control module is configured to determine the probability mapping based on a transformation between the coordinate system of the at least one display device and the coordinate system of the at least one image-recording device.

13. The system of claim 12, wherein the at least one control module is configured to determine the probability mapping based on a radiometric calibration between the at least one display device and the respective image-recording device.

14. The system of claim 12, wherein a plurality of calibration marks are arranged on the at least one display device, which are detectable by the at least one image-recording device to facilitate the transformation between the coordinate system of the at least one display device and the coordinate system of the at least one image-recording device.

15. The system of claim 10, wherein the at least one control module is configured to insert calibration information into the sequence of display information, and wherein the at least one display device is configured to display the calibration information.

16. The system of claim 15, wherein the calibration information comprises at least a single monochrome image, wherein the image has a display duration of at least one or precisely one frame, and wherein the image has a color having a high contrast to a foreground object.

17. A method for dynamically maximizing thy: contrast between the foreground and background in images and/or image sequences, the method comprising:
    detecting at least one image by at least one image-recording device;
    calculating a transformation between a two-dimensional coordinate system of the at least one image-recording device and a two-dimensional coordinate system of at least one display device;
    carrying out a segmentation to determine at least occlusions of background objects through foreground objects in an image;
    displaying display information, including video clips, on the at least one display device, wherein the display information displayed on the at least one display device is recorded by the at least one image-recording device;
    during the segmentation, identifying quality data on the segmentation and adjusting the display information displayed on the at least one display device based on the quality data;
    providing a stored sequence of display information to be displayed on the at least one display device one after the other; and
    determining for remaining display information of the sequence, in which display information an expected probability distribution of the foreground and an expected probability distribution of the background of the image-recording device differ the most.

* * * * *